(12) United States Patent
Zhang

(10) Patent No.: US 10,945,631 B2
(45) Date of Patent: Mar. 16, 2021

(54) MAGNET ASSEMBLY FOR MAGNETIC RESONANCE IMAGING (MRI) SCANNING SYSTEM

(71) Applicant: SIGWA COMPANY, LLC, Acton, MA (US)

(72) Inventor: Fengling Zhang, Acton, MA (US)

(73) Assignee: Sigwa Company, LLC, Acton, MA (US)

( * ) Notice: Subject to any disclaimer, the term of this patent is extended or adjusted under 35 U.S.C. 154(b) by 0 days.

(21) Appl. No.: 16/515,651

(22) Filed: Jul. 18, 2019

(65) Prior Publication Data
US 2021/0015394 A1 Jan. 21, 2021

(51) Int. Cl.
| | | |
|---|---|---|
| A61B 5/055 | (2006.01) | |
| G01R 33/36 | (2006.01) | |
| G01R 33/385 | (2006.01) | |

(52) U.S. Cl.
CPC .......... *A61B 5/055* (2013.01); *G01R 33/3614* (2013.01); *G01R 33/3852* (2013.01)

(58) Field of Classification Search
CPC . A61B 5/055; G01R 33/3614; G01R 33/3852
See application file for complete search history.

(56) References Cited

U.S. PATENT DOCUMENTS

| | | | |
|---|---|---|---|
| 5,431,165 A | 7/1995 | Sellers | |
| 5,680,086 A | 10/1997 | Allis et al. | |
| 5,825,187 A | 10/1998 | Ohashi et al. | |
| 6,670,877 B2 * | 12/2003 | Rapoport | G01R 33/3873 324/320 |
| 6,707,359 B2 | 3/2004 | Yoshida et al. | |
| 7,116,198 B1 | 10/2006 | Abele | |
| 7,262,678 B2 * | 8/2007 | Tan | G01R 33/3806 335/296 |
| 7,463,129 B1 * | 12/2008 | Danby | G01R 33/3802 335/216 |
| 9,666,345 B1 * | 5/2017 | Honein | H01F 6/06 |
| 9,709,653 B2 | 7/2017 | Wheaton et al. | |
| 2007/0010702 A1 * | 1/2007 | Wang | A61F 2/82 600/8 |
| 2017/0035465 A1 * | 2/2017 | Robinson | A61B 17/7052 |
| 2018/0313920 A1 | 11/2018 | Sotgiu | |

FOREIGN PATENT DOCUMENTS

WO 2013024257 2/2013

* cited by examiner

*Primary Examiner* — Akm Zakaria
(74) *Attorney, Agent, or Firm* — Kanika Radhakrishnan; Evergreen Valley Law Group

(57) ABSTRACT

The present disclosure provides a magnet assembly for a Magnetic Resonance Imaging (MRI) system. The assembly includes a yoke having a frame member movably positioned by a magnet movement unit. A first arm extends laterally from a first end of the frame member and includes a first magnet-pole assembly having a first central axis. A second arm extends laterally from a second end of the frame member and includes a second magnet-pole assembly. The second magnet-pole assembly includes a second central axis and configured to orient towards with the first magnet-pole assembly while maintaining a gap therebetween, for positioning a body portion for magnetization. A first and a second clamp member are each mounted about a peripheral side surface of the magnet-pole assemblies, respectively. The clamp members are configured to attenuate a leakage flux emanating from the magnet pole assemblies.

8 Claims, 11 Drawing Sheets

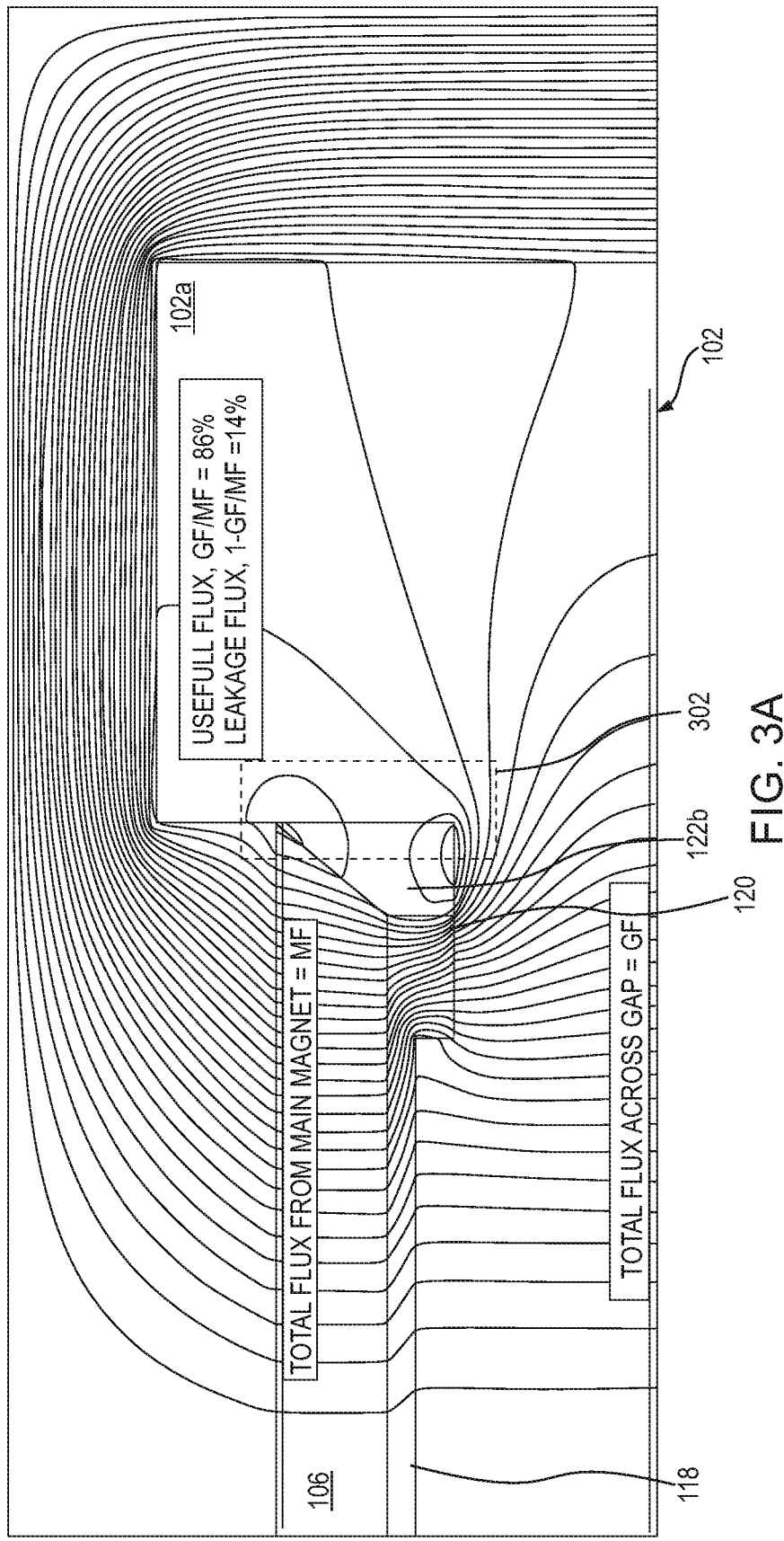

MAGNET ASSEMBLY FOR MAGNETIC RESONANCE IMAGING (MRI) SCANNING SYSTEM

TECHNICAL FIELD

The present disclosure relates generally to a magnet assembly for a Magnetic resonance imaging (MRI) scanning system and, more particularly to, the magnet assembly for an equine MRI scanning system.

BACKGROUND

In the medical field, imaging techniques, such as MRI techniques, are typically used for generating visual representations of the anatomy of a body of a subject for clinical analysis and medical intervention. The MRI technique generates detailed spatial images of the body, enabling accurate and precise medical diagnosis by a medical practitioner. The MRI technique is typically employed to the subject via MRI scanners or devices.

The MRI scanners generally include a large magnet surrounding a cylindrical tunnel, in which the subject is positioned. The subject is required to remain still for a predetermined duration of time for scanning a body portion. Hence, these MRI scanners are typically employed for human subjects, due to the requirement of subject cooperation. As such, these MRI scanners are unsuitable for imaging subjects such as equines or similar large animals, since such subjects i.e. animals do not ordinarily cooperate during the MRI scanning. The medical practitioner may, therefore, administer anesthesia to the animal, for ensuring cooperation during the procedure. Administering anesthesia to subjects, particularly to animals, may carry significant risk to the health of the animals. Moreover, the dimensions of the MRI scanner may not be sufficiently large for accommodating the animal and thus the MRI scanner may only be able to scan extremities of limbs of the animal.

To overcome the aforesaid limitation in scanning the animals, the MRI devices using permanent magnets may be configured with flat magnetic plates (consisting of permanent magnetic materials, such as Neodymium Iron Boron NdFeB, or etc.) of the required size and held together by a support structure. The flat magnetic plates may be spaced apart by a predetermined distance for allowing the animal to be positioned therebetween. The flat magnets provide required magnetic field strength for interaction with the body portion of the animal for generating the visual representation. Additionally, due to the gap maintained between plates, the animal may be positioned suitably between the flat magnetic plates for generating the visual representation. As an example, for scanning a left-front limb of a horse, the horse may be positioned such that the left-front limb is positioned between the magnetic plates. The support structure is thereafter maneuvered suitably for generating the visual representation of the front-left limb of the horse.

However, these MRI scanners face issue of a predominant flow of leakage flux within the flat magnets, which affects the imaging performance. Although the flow of the leakage flux may be compensated by installing larger magnets, using greater amount of permanent magnetic materials, for greater magnetic field strengths, the resulting magnet assembly will be bulky, expensive and cumbersome for handling, which is undesirable. Additionally, due to the flow of leakage flux, the flux available for magnetic interaction with the body portion decreases, which inherently decreases imaging performance and requires the longer imaging times. Such prolonged imaging times make it more likely that the animal will move during the imaging, making the images non-diagnostic. Moreover, due to metallic parts installed in the MRI scanner along with the magnets, the magnets may generate eddy current which further deteriorates the image performance of the MRI scanner.

Therefore, there is a need for techniques which can overcome one or more limitations stated above in addition to providing other technical advantages.

SUMMARY

Various embodiments of the present disclosure provide a magnet assembly for a Magnetic Resonance Imaging (MRI) system. The assembly includes a yoke having a frame member movably positioned relative to the floor by a magnet movement unit (MMU). The frame member is mounted to the MMU. The MMU is a mechanism that can move the frame member in any of several directions or as per design requirements. The MMU can be attached to the top of the floor, attached into the floor, or attached to other structural features not at floor level. A first arm extends laterally from a first end of the frame member and includes a first magnet-pole assembly. The first magnet-pole assembly includes a first central axis. A second arm extends laterally from a second end of the frame member and includes a second magnet-pole assembly. The second magnet-pole assembly includes a second central axis and is configured to orient towards the first magnet-pole assembly while maintaining a gap therebetween for positioning a body portion of a subject for imaging. A first clamp member and a second clamp member are each mounted about a peripheral side surface of the first magnet-pole assembly and the second magnet-pole assembly, respectively. The first and the second clamp members are configured to attenuate a leakage flux emanating from the first magnet-pole assembly and the second magnet pole assembly, respectively.

In another embodiment, the magnet assembly for an equine MRI system is disclosed. The assembly includes the yoke having the frame member movably positioned relative to the floor by a magnet movement unit (MMU). The frame member is mounted to the MMU. The MMU can move the frame member in any of several directions or as per design requirements. The first arm extends laterally from the first end of the frame member and includes the first magnet-pole assembly. The first magnet-pole assembly includes the first central axis. The second arm extends laterally from the second end of the frame member and includes the second magnet-pole assembly. The second magnet-pole assembly includes the second central axis and is configured to orient towards the first magnet-pole assembly while maintaining the gap therebetween for positioning the body portion of a subject for imaging. The frame member, the first arm and the second arm conform to a fork-like structure. The first clamp member and the second clamp member are each mounted about the peripheral side surface of the first magnet-pole assembly and the second magnet-pole assembly, respectively. The first and the second clamp members are configured to attenuate a leakage flux emanating from the first magnet-pole assembly and the second magnet pole assembly, respectively.

In another embodiment, an equine MRI system is disclosed. The system includes the yoke including the frame member movably positioned relative to the floor by a magnet movement unit (MMU). The frame member is mounted to the MMU. The MMU can move the frame member in any of several directions or as per design requirements. The frame member is rotatably connectable to a guide rail extending laterally from the MMU. The guiderail is configured to rotatably receive the frame member and allow rotational movement of the frame member about the MMU between a first angle position and a second angle position. This rotation allows the magnet gap to be parallel with the floor. This way an anesthetized animal can be brought in a gurney and allow the animal's leg to be imaged. The first arm extending laterally from the first end of the frame member and including a first magnet-pole assembly. The first magnet-pole assembly includes a first magnet, a first pole shoe and a first pole ring. The first magnet includes a top surface and a medial surface, wherein the top surface of the first magnet is mounted to the medial surface of the first arm of the yoke. The first pole shoe is mounted along a periphery of the medial surface of the first magnet. The first pole ring is mounted to the first pole shoe and configured to conduct magnetic field emanating from the first magnet along the exposed surface of the first pole ring. The second arm extends laterally from the second end of the frame member and includes a second magnet-pole assembly. The second magnet-pole assembly includes the second central axis and is configured to orient towards the first magnet-pole assembly while maintaining a gap therebetween for positioning a body portion of a subject for imaging. The second magnet-pole assembly includes a second magnet, a second pole shoe and a second pole ring. The second magnet includes a medial surface and a bottom surface, wherein the medial surface of the second magnet mounted to the medial surface of the second arm of the yoke. The second pole shoe is mounted about a periphery of the medial surface of the second magnet. The second pole ring is mounted to the second pole shoe, the second pole ring configured to conduct magnetic field emanating from the second magnet along the exposed surface of the second pole ring. The frame member, the first arm and the second arm conform to a fork-like structure. The first clamp member and the second clamp member are each mounted about a peripheral side surface of the first magnet-pole assembly and the second magnet-pole assembly, respectively. The first and the second clamp members are configured to attenuate a leakage flux emanating from the first magnet-pole assembly and the second magnet pole assembly, respectively. The first and the second clamp members are magnetized in a direction perpendicular to a magnetization direction of the first magnet-pole assembly and the second magnet-pole assembly, respectively. An eddy current control plate made of a permeable layer is mounted onto each of the first magnet and the second magnet via a magnetic layer. The eddy current control plate is configured to attenuate eddy current generated around the first magnet and the second magnet. Further, a first retainer member and a second retainer member are each mounted on the first and the second clamp members, respectively. The first and the second retainer members are configured to maintain position of the first and the second clamp members on each of the first magnet-pole assembly and the second magnet-pole assembly, respectively. In another embodiment, the magnet assembly has a non-uniform configuration of the magnet so that the magnets are configured with a reduced thickness in the center and a thicker section at the periphery of the magnet to achieve a more compact magnet design. The computing device is configured to process the magnetic field interaction with the body portion positioned between the first magnet-pole assembly and the second magnet-pole assembly for generating a visual representation of an anatomy of the body portion.

BRIEF DESCRIPTION OF FIGURES

The following detailed description of illustrative embodiments is better understood when read in conjunction with the appended drawings. For the purpose of illustrating the present disclosure, exemplary constructions of the disclosure are shown in the drawings. However, the present disclosure is not limited to a specific device or a tool and instrumentalities disclosed herein. Moreover, those in the art will understand that the drawings are not to scale. Wherever possible, like elements have been indicated by identical numbers:

FIG. 3A is a schematic view depicting the magnetic field distribution in the magnet assembly, in accordance with an example embodiment of the present disclosure;

Figure 1A:
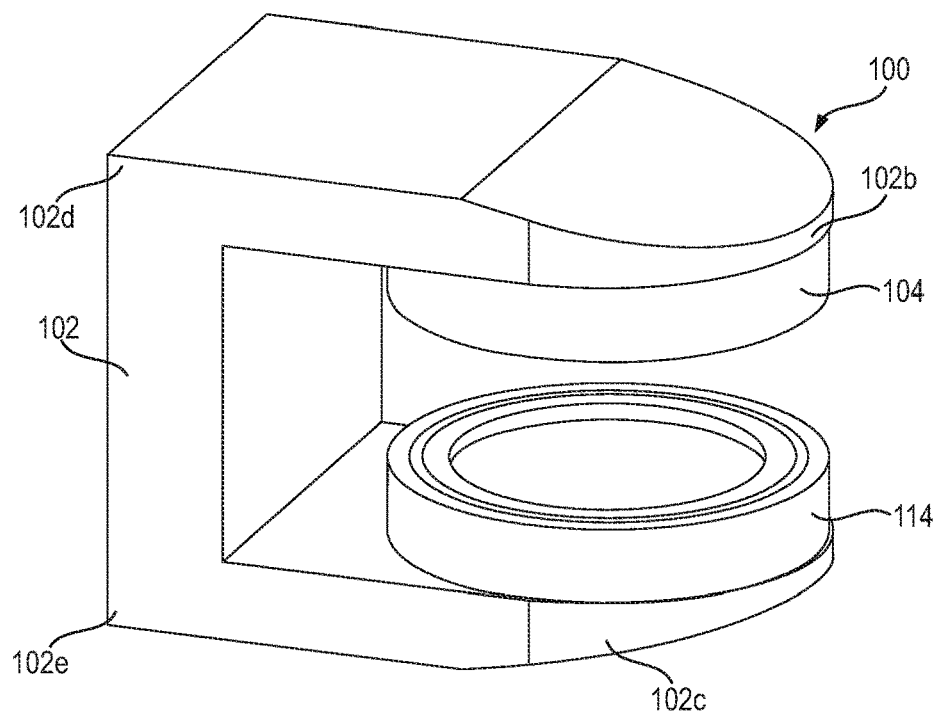
FIG. 1A is a perspective view of a magnet assembly for a Magnetic Resonance Imaging (MRI) scanning system, in accordance with an example embodiment of the present disclosure.

The drawings referred to in this description are not to be understood as being drawn to scale except if specifically noted, and the drawings are only exemplary in nature.

DETAILED DESCRIPTION

In the following description, for purposes of explanation, numerous specific details are set forth in order to provide a thorough understanding of the present disclosure. It will be apparent, however, to one skilled in the art that the present disclosure can be practiced without these specific details. Descriptions of well-known components and processing techniques are omitted so as to not unnecessarily obscure the embodiments herein. The examples used herein are intended merely to facilitate an understanding of ways in which the embodiments herein may be practiced and to further enable those of skill in the art to practice the embodiments herein. Accordingly, the examples should not be construed as limiting the scope of the embodiments herein.

Reference in this specification to "one embodiment" or "an embodiment" means that a particular feature, structure, or characteristic described in connection with the embodiment is included in at least one embodiment of the present disclosure. The appearance of the phrase "in an embodiment" in various places in the specification are not necessarily all referring to the same embodiment, nor are separate or alternative embodiments mutually exclusive of other embodiments. Moreover, various features are described which may be exhibited by some embodiments and not by others. Similarly, various requirements are described which may be requirements for some embodiments but not for other embodiments.

Moreover, although the following description contains many specifics for the purposes of illustration, anyone skilled in the art will appreciate that many variations and/or alterations to said details are within the scope of the present disclosure. Similarly, although many of the features of the present disclosure are described in terms of each other, or in conjunction with each other, one skilled in the art will appreciate that many of these features can be provided independently of other features. Accordingly, the description of the present disclosure is set forth without any loss of generality to, without imposing limitations upon, the present disclosure.

Overview

Various embodiments of the present disclosure provide a magnet assembly for a Magnetic Resonance Imaging (MRI) scanning system. Particularly, the movable frame member of the magnet assembly is configured to be mountable onto the magnet movement unit (MMU) of the equine MRI scanning system, for scanning a body portion of a horse or an equine. The MRI magnet is configured to reduce leakage flux therein, for improved imaging performance. The reduction in the leakage flux inherently increases the magnetic flux usable for imaging the body portion. As such, reducing the size of the magnets required in the system, renders a compact magnet assembly.

The MRI magnet assembly includes a yoke comprising a frame member movably positioned relative to the floor by a magnet movement unit (MMU). The frame member is mounted to the MMU. The MMU can move the frame member in any of several directions or as per design requirements. The frame member may be movably mounted onto the MMU via a bearing mounted to a guiderail extending laterally from the MMU. In one configuration, components for making the MMU may be available from companies such as INA, PCB Linear, Bishop Wisecarver, and HIWIN. The frame member may be moved between a first position and second position for magnetizing the body portion of the subject to generate a visual representation, for medical diagnosis. The yoke also includes a first arm and a second arm extending laterally from a first end and a second end of the frame member respectively. The first arm and the second arm may extend from the frame member to form a fork-like structure or a C-shaped structure or a horse-shoe magnet structure. The first arm includes a first magnet-pole assembly having a first central axis and configured to magnetize the body portion of the subject. The first magnet-pole assembly includes a first magnet having a top surface and a medial surface. The top surface of the first magnet is mounted to the medial surface of the first arm. A first pole shoe is mounted along the periphery of the medial surface of the first magnet and is configured to receive a first pole ring. The first pole ring is configured to conduct the magnetic field emanating from the first magnet along its exposed surface. This configuration ensures that the magnetic field strength is maximum at the periphery of the first magnet while being uniform about its center.

Further, the second arm includes a second magnet-pole assembly having a second central axis and configured to magnetize the body portion of the subject. The second magnet-pole assembly is oriented towards the first magnet-pole assembly, while maintaining a gap therebetween for positioning the body portion of the subject. The second magnet-pole assembly, similar to the first magnet-pole assembly includes a second magnet having a medial surface and a bottom surface. The bottom surface of the second magnet is mounted to the medial surface of the second arm. A second pole shoe is mounted along the periphery of the medial surface of the second magnet and is configured to receive the second pole ring. The second pole ring is configured to conduct the magnetic field emanating from the second magnet along its exposed surface. This configuration of the first magnet and the second magnet ensures that the body portion is exposed to suitable magnetization for generating the optimum visual representation. Further, a first clamp member and a second clamp member made of permanent magnet material encompass a peripheral side surface of the first magnet-pole assembly and the second magnet-pole assembly, respectively. The first and the second clamp members may be configured with a thinner dimension towards the arms of the yoke and a thicker dimension towards the pole rings of the magnet-pole assembly. The first and the second clamp members are configured to attenuate the leakage flux generated in the first magnet and the second magnet, thereby improving the usable magnetic flux for magnetizing the body portion. A first retainer member and a second retainer member may be configured on the outer circumference of the first and the second clamp members respectively, for fastening the first and the second clamp members onto the respective magnet-pole assemblies. An eddy current control plate, generally made from amorphous silicon iron laminations, traditionally, has added gaps to avoid saturation by the main magnet flux. The added gaps under the eddy control plate decrease the main field of the MRI magnet. The disclosed device advantageously fills these needs and addresses the aforementioned deficiencies by providing a magnetic material layer, herein called Flux Saturation Control Plate (FSCP), in back of the eddy current control plate. The Flux Saturation Control Plate (FSCP) is made from tiles of permanent magnet material (such as NdFeB) and is sized to lower the saturation of the amorphous silicon iron while boosting the main magnet field. The Flux Saturation Control Plate (FSCP) is oriented to boost the main field of the MRI magnet. One Flux Saturation Control Plate (FSCP) is bonded onto each of the first pole shoe and a second pole shoe, and the eddy current control plate is then mounted onto each of the Flux Saturation Control Plate (FSCP). This Flux Saturation Control Plate (FSCP) may extend radially from the central axis of the first magnet-pole assembly and the second magnet-pole assembly, up to the respective pole rings. This configuration of the eddy current control plate is configured to attenuate the eddy currents generated during imaging.

Further, a computing device is associated or communicably coupled with the first magnet-pole assembly, the second magnet-pole assembly and the body portion of the subject, for processing the magnetic field interaction therebetween. The computing device upon processing is configured to generate the visual representation for indicating the anatomy of the body portion.

The present disclosure also provides an equine MRI scanning system employing the magnet assembly for imaging the body portion of the subject. The MRI scanning system includes the computing device, for processing the magnetic interaction between the magnet assembly and the body portion. The magnetic interaction is processed suitably by the computing device for generating the visual representation of the anatomy of the body portion.

Figure 1B:
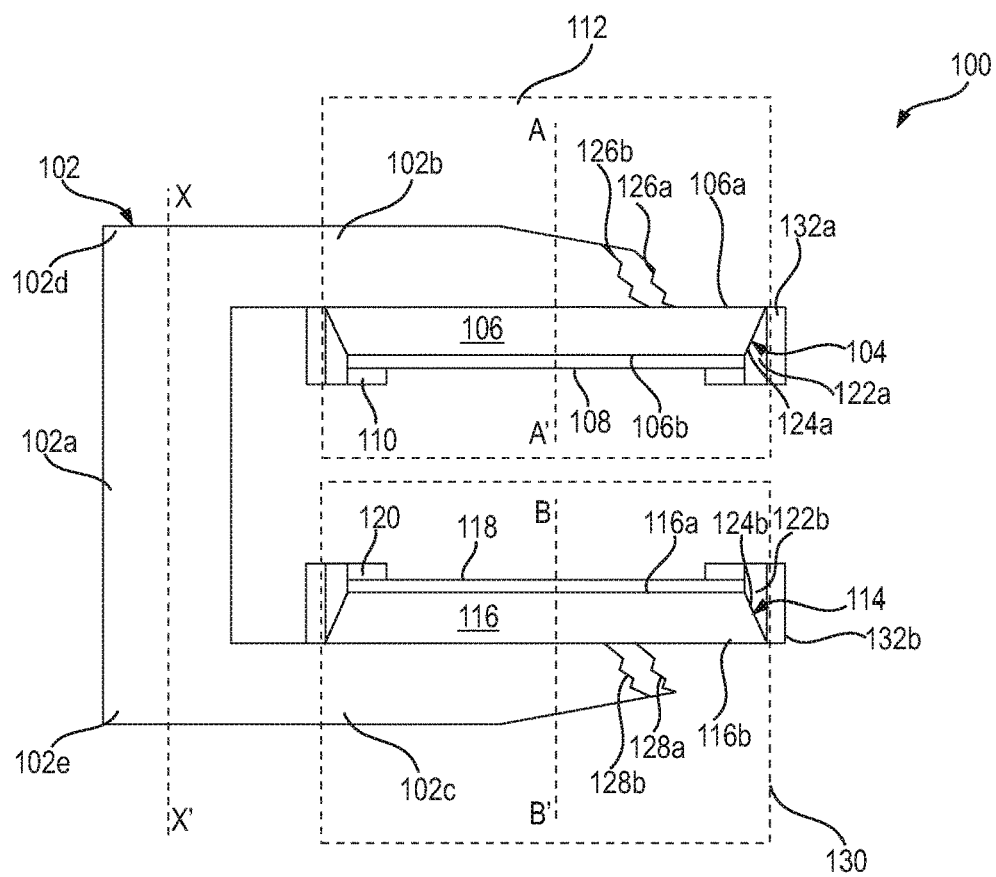
FIG. 1B is a cross section view of the magnet assembly of FIG. 1A, in accordance with an example embodiment of the present disclosure.
Figure 9:
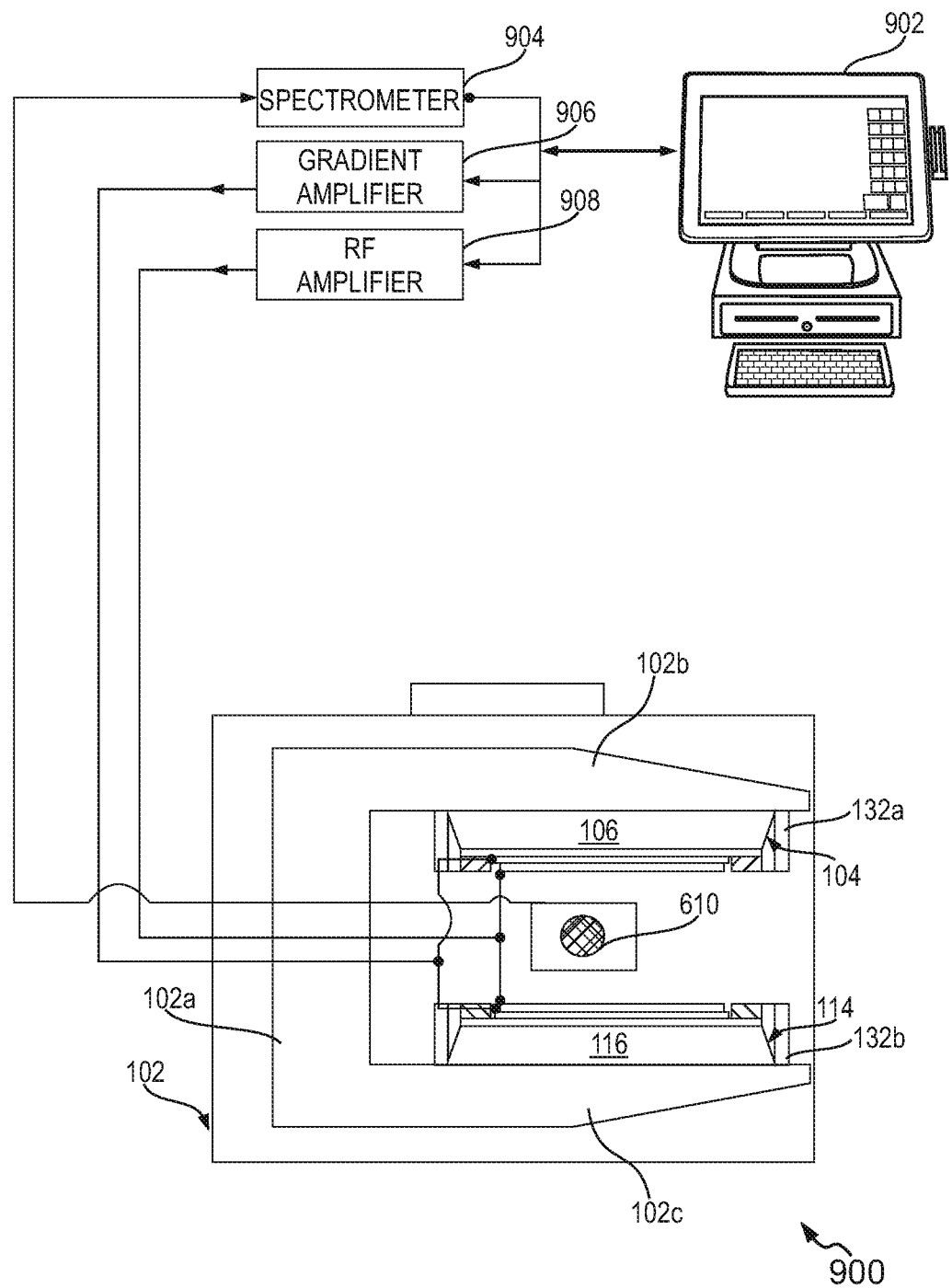
FIG. 9 is a schematic view of an equine MRI system employing the magnet assembly, in accordance with an example embodiment of the present disclosure.

Various embodiments of a magnet assembly for a Magnetic Resonance Imaging (MRI) system are explained in a detailed manner, herein with reference to FIG. 1A-1B to FIG. 9.

FIGS. 1A and 1B, in one exemplary embodiment of the present disclosure, illustrate a magnet assembly 100 for a Magnetic Resonance Imaging (MRI) system. The magnet assembly 100 is configured to attenuate leakage flux, thereby improving the magnetic field strength and the imaging performance.

Figure 6:
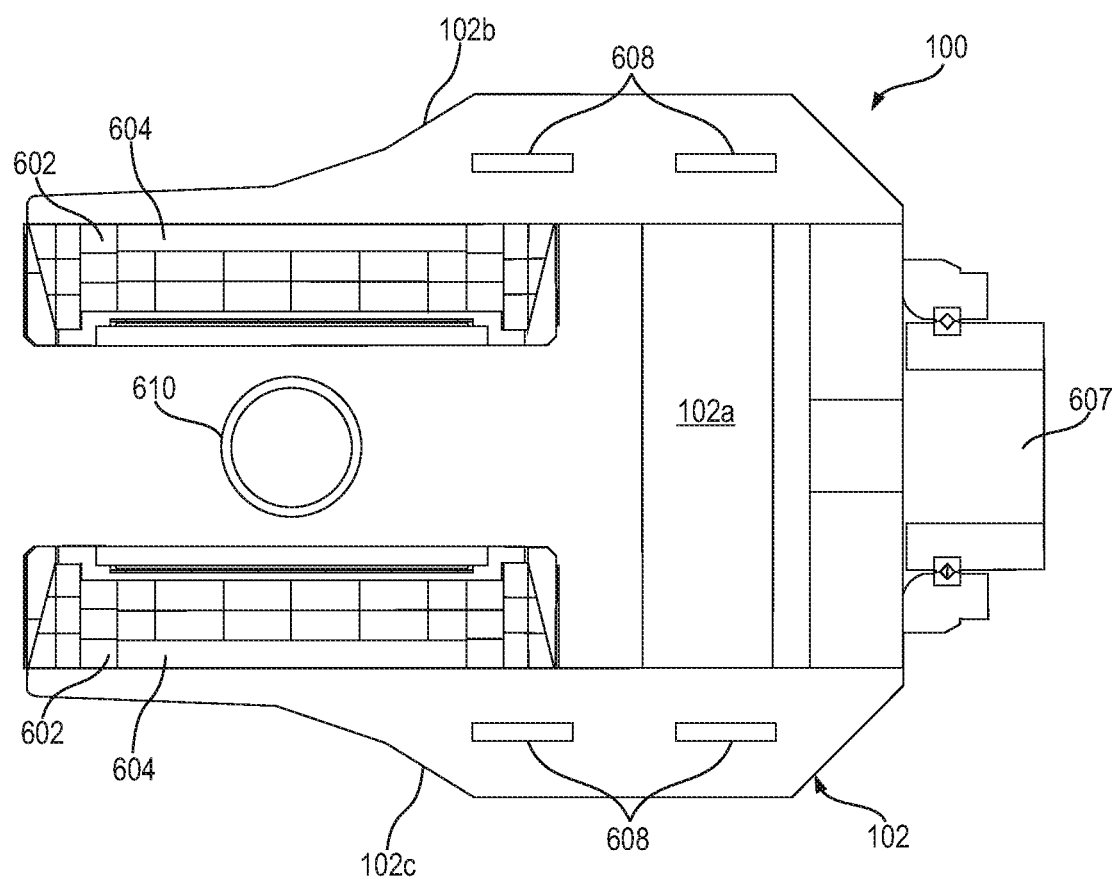
FIG. 6 is a schematic view of the magnet assembly depicting a first magnet and a second magnet fabricated via a plurality of magnetic blocks, in accordance with an example embodiment of the present disclosure.
Figure 7A:
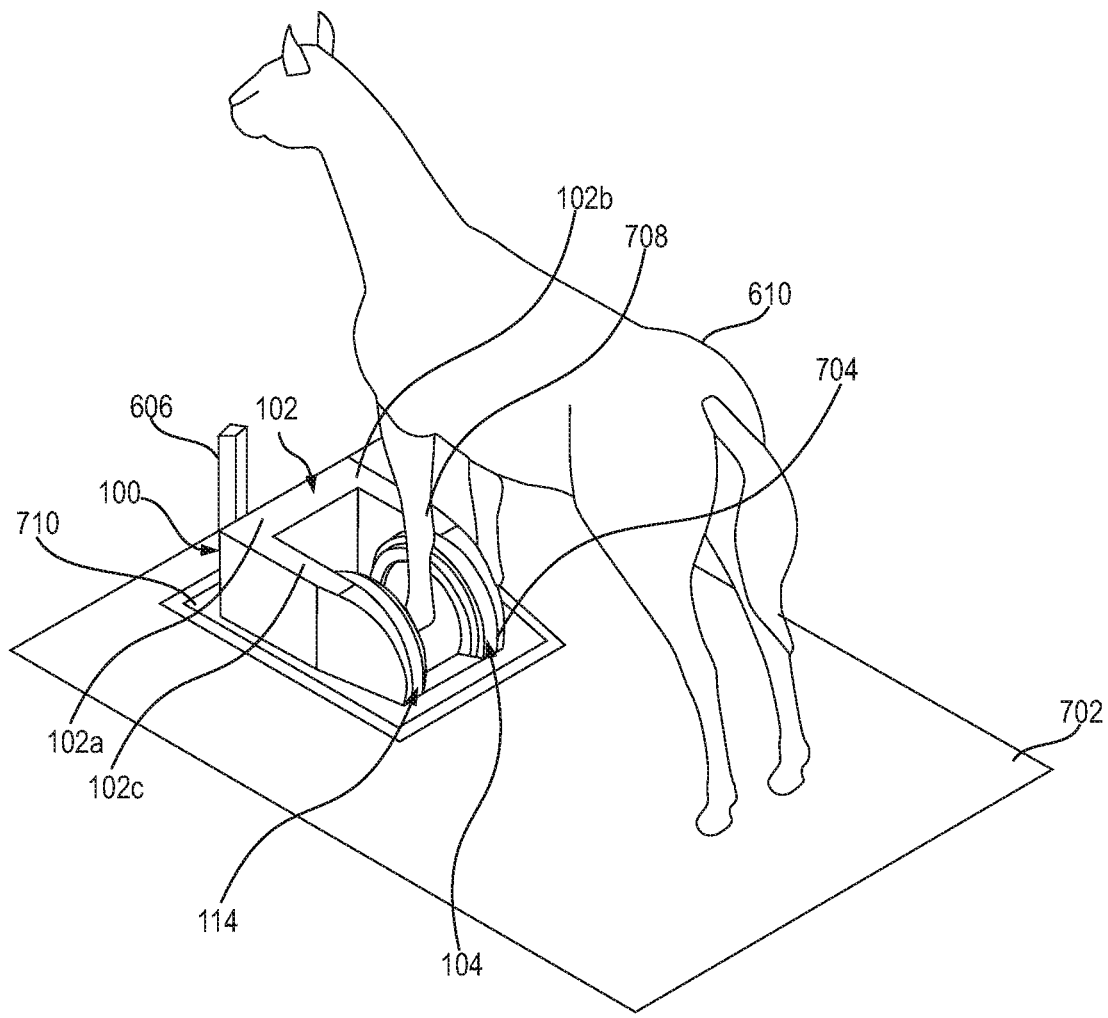
FIG. 7A is a schematic view of the magnet assembly in use for scanning a body portion of a subject, in accordance with an example embodiment of the present disclosure.
Figure 7B:
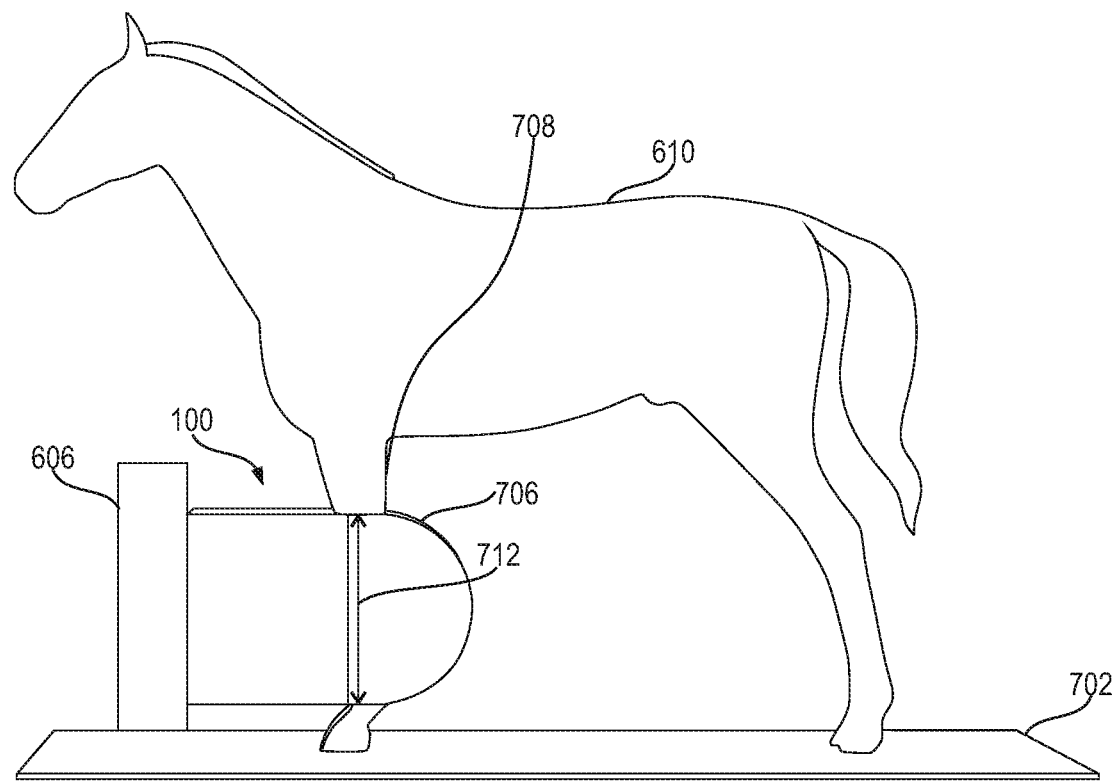
FIG. 7B is a schematic view of the magnet assembly in use for scanning the body portion of the subject, in accordance with another example embodiment of the present disclosure.

The magnet assembly 100 includes a yoke 102, configured to act as a support structure for all the components of the assembly 100. The yoke 102 includes a frame member 102a movably positioned relative to the floor by a magnet movement unit (MMU). The frame member is mounted to the MMU. (not shown in FIGS. 1A-1B). The MMU can move the frame member in any of several directions or as per design requirements. The frame member can be movably mounted to the MMU. The frame member 102a may be a slab-like structure, configured to be mounted on a guiderail 607 (for e.g. as shown in FIG. 6) to also extending laterally from the MMU 606 (for e.g. as shown in FIG. 7A). The frame member 102a accordingly is movable between a first position 704 (for e.g. as shown in FIG. 7A) and a second position 706 (for e.g. as shown in FIG. 7B), which is further explained in detail. In one configuration, the frame member 102a may be configured with a cross-section selected from one of a square cross-section, a circular cross-section or any other cross-section as per design feasibility and requirement. In one implementation, the frame member 102a is a slab configured with a rectangular cross-section. The frame member 102a is made of materials such as but not limited to ferrous material or any other material which serves the purpose of conducting the magnetic field.

The yoke 102 further includes a first arm 102b extending laterally from a first end 102d of the frame member 102a. The first arm 102b may either be an integral component of the frame member 102a or may be mounted onto the first end 102d via conventional mounting means, as per design feasibility and requirement. In one implementation, the first arm 102b may be configured with dimensions in conformity with the dimensions of the frame member 102a for ensuring a unibody construction (as shown in FIG. 1A). The first arm 102b includes a first magnet-pole assembly 104. As such, the length of extension or dimensions of the first arm 102b may be considered based on the size of the first magnet-pole assembly 104 or as per design feasibility and requirement.

The first magnet-pole assembly 104 includes a first magnet 106 having a top surface 106a and a medial surface 106b.

The first magnet 106 is mounted onto the medial surface 126a of the first arm 102b via the top surface 106a, such that a first central axis A-A' of the first magnet 106 is parallel to an internal axis X-X' of the frame member 102a. The first arm 102b is bisected angularly, in FIG. 1B for enabling visualization of the medial surface 126a. In one configuration, the first central axis A-A' of the first magnet 106 may be oriented or inclined with respect to the internal axis X-X' as per design feasibility and requirement. The first magnet 106 may be mounted onto the first arm 102b via mounting means selected from one of an adhesive bonding, a fastening, a clamping and the like as per feasibility and requirement. Further, the first magnet 106 may be a cylindrical structure of unibody construction (for e.g. as shown in FIGS. 1A and 1B) or may be a fabrication of plurality of magnetic blocks 602 (for e.g. as shown in FIG. 6). The first magnet 106 may be magnetized or subjected to magnetization prior to its mounting on the first arm 102b. The magnetization ensures maximum output and stability in the magnetic field emanating from the first magnet 106. The magnetization may be carried out via conventional techniques, i.e. by introducing magnetic field of required intensity or any other techniques as per feasibility and requirement. The magnetization direction of the first magnet 106 may be selected, based on the direction of flow of the magnetic field, upon mounting onto the first arm 102b. In one configuration, the first magnet 106 may be a cylindrical structure with cross-section selected to be one of a circular cross-section, a square cross-section, a rectangular cross section or any of other cross-sections as per design feasibility and requirement.

In one implementation, a plurality of magnetic blocks 602 (for e.g. as shown in FIG. 6) of sintered Neodymium Iron Boron (NdFeB) magnet material are bonded suitably for the first magnet 106. The magnetic blocks 602 may be configured with a dimension of 'ten' inches as diameter and about 'four' inches as width (or thickness) in a magnetizing direction. The resulting first magnet 106 made of the Neodymium Iron Boron (NdFeB) magnet material may be characterized with a tolerance of 3% in magnetic strength and 3° in the magnetization direction.

The first magnet-pole assembly 104 includes a first pole shoe 108 mounted to the medial surface 106b of the first magnet 106. The first pole shoe 108 is positioned along the periphery of the medial surface 106b. The first pole shoe 108 may be configured with a socket means (not shown in Figures) or a holding means for receiving a first pole ring 110. The first pole ring 110 may be a ring like structure, connectable onto the first pole shoe 108. The first pole ring 110 is configured for conducting the magnetic field emanating from the first magnet 106 around its exposed surface. As such, the magnetic field strength is maintained to be uniform at the vicinity of the central axis A-A' by adding field at the periphery or outer circumference of the first magnet 106. The first pole shoe 108 and the first pole ring 110 may be made of ferrous materials or any other materials suitable for conducting the magnetic field from the first magnet 106. Further, the first magnet 106, the first arm 102b, the first pole shoe 108 and the first pole ring 110 constitute a first pole 112 of the yoke 102.

The yoke 102 further includes a second arm 102c extending laterally from a second end 102e of the frame member 102a. The second arm 102c may either be an integral component of the frame member 102a or may be mounted onto the second end 102e via conventional mounting means, as per design feasibility and requirement. In one implementation, the second arm 102c may be configured with dimensions in conformity with the dimensions of the frame member 102a for ensuring a unibody construction. The second arm 102c may also be configured with a length equivalent to the length of the first arm 102b. The second arm 102c includes a second magnet-pole assembly 114. As such, the length of extension or dimensions of the second arm 102c may be considered based on the size of the second magnet-pole assembly 114 or as per design feasibility and requirement. The second magnet-pole assembly 114 is configured to orient towards the first magnet-pole assembly 104 while maintaining a gap therebetween. The gap ensures positioning of a body portion 708 (for e.g. as shown in FIG. 7A) of a subject 610 (for e.g. as shown in FIG. 7A) for magnetization. As such, the dimension of the gap is configured such that, the body portion 708 of the subject 610 is positioned between the first magnet-pole assembly 104 and the second magnet-pole assembly 114. This configuration ensures that the assembly 100 can accommodate the subject of any size, for scanning and generating the visual representation. In another embodiment, the first arm 102b and/or the second arm 102c may be slidably mounted on the frame member 102a (not shown in Figures), so that the dimension of the gap is altered as per feasibility and requirement. The second magnet-pole assembly 114 may be configured to be a mirror image of the first magnet-pole assembly 104 or is symmetrical about a mid-plane (not shown in Figures) extending laterally to the frame member 102a.

The second magnet-pole assembly 114 includes a second magnet 116 having a medial surface 116a and a bottom surface 116b. The second magnet 116 is mounted to the medial surface 128a of the second arm 102c via the bottom surface 116b, such that a second central axis B-B' of the second magnet 116 is parallel to an internal axis X-X' of the frame member 102a. The second arm 102c is bisected angularly, in FIG. 1B for enabling visualization of the medial surface 128a. In one configuration, the central axis B-B' of the second magnet 116 may be oriented or inclined with respect to the internal axis X-X' as per design feasibility and requirement. The second central axis B-B' is also aligned coaxially to the first central axis A'A'. The second magnet 116 may be mounted onto the second arm 102c via the mounting means selected from one of the adhesive bonding, the fastening, the clamping and the like as per feasibility and requirement. Further, the second magnet 116 may be a cylindrical structure of unibody construction (for e.g. as shown in FIGS. 1A and 1B) or may be a fabrication of plurality of magnetic blocks 602 (for e.g. as shown in FIG. 6). The second magnet 116 may be magnetized or subjected to magnetization prior to its mounting on the second arm 102c. The magnetization ensures maximum output and stability in the magnetic field emanating from the second magnet 116. The magnetization may be carried out via conventional techniques, i.e. by introducing magnetic field of required intensity or any other techniques as per feasibility and requirement. The magnetization direction of the second magnet 116 may be selected, based on the direction flow of the magnetic field, upon mounting onto the second arm 102c. In one configuration, the second magnet 116 may be a cylindrical structure with cross-sections selected to be one of a circular cross-section, a square cross-section, a rectangular cross section or any of other cross-sections as per design feasibility and requirement.

The second magnet-pole assembly 114 includes a second pole shoe 118 mounted to the medial surface 116a of the second magnet 116. The second pole shoe 118 is positioned along the periphery of the medial surface 116a. The second shoe 118 may be configured with a socket means (not shown in Figures) or a holding means for receiving a second pole ring 120. The second pole ring 120 may be a ring like structure, connectable onto the second pole shoe 118. The second pole ring 110 is configured for conducting the magnetic field emanating from the second magnet 116 around its exposed surface. As such, the magnetic field strength is maintained to be uniform at the vicinity of the second central axis B-B' by adding field at the periphery or outer circumference of the second magnet 116. The second pole shoe 118 and the second pole ring 120 may be made of ferrous materials or any other materials suitable for conducting the magnetic field from the second magnet 116. Further, the second magnet 116, the second arm 102c, the second pole shoe 118 and the second pole ring 120 constitute a second pole 130 of the yoke 102.

In one implementation, a plurality of magnetic blocks 602 of sintered Neodymium Iron Boron (NdFeB) magnet material are bonded suitably for the second magnet 116. The magnetic blocks 602 may be configured with a dimension of 'ten' inches as diameter and about 'four' inches as width (or thickness) in a magnetizing direction. The resulting second magnet 116 made of the Neodymium Iron Boron (NdFeB) magnet material may be characterized with a tolerance of 3% in magnetic strength and 3% in the magnetization direction.

In one implementation, the first arm 102b and the second arm 102c are mounted to the frame member 102a such that a magnetic conductive path is formed therebetween. As such, the magnetic field emanating from the first pole 112 via the first magnet 106 traverses through the frame member 102a to the second pole 130. Similarly, the magnetic field emanating from the second pole 130 traverses through the frame member 102a to the first pole 112.

In one configuration, due to the traversal of magnetic field towards the frame member 102a, the lateral surface 126b of the first arm 102b may be configured to a tapered construction, with the thickness at the edges being thinner. This configuration ensures ease of maneuverability of the assembly 100 during operation for scanning the body portion 708 of the subject 610.

In another configuration, due to the traversal of magnetic field towards the frame member 102a, the lateral surface 128b of the second arm 102c may be configured to a tapered construction, with the thickness at the edges being thinner. This configuration ensures ease of maneuverability of the assembly 100 during operation for scanning the body portion 708 of the subject 610.

The assembly 100 further comprises a first clamp member 122a encompassing a peripheral side surface 124a of the first magnet-pole assembly 104. The assembly 100 also includes a second clamp member 122b encompassing a peripheral side surface 124b of the second magnet-pole assembly 114. The first and the second clamp members 122a, 122b are configured to attenuate leakage flux flowing through the yoke 102. For ease of understanding, the first and the second clamp members 122a, 122b are hereinafter interchangeably referred to as 'clamp members 122a, 122b'. The clamp members 122a, 122b are made of permanent magnetic material such as, but not limited to, Neodymium Iron Boron (NdFeB) magnet material or any other material as per design feasibility and requirement.

The clamp members 122a, 122b are magnetized via the conventional magnetization means, prior to attachment with the peripheral side surfaces 124a, 124b. The magnetization allows the clamp members 122a, 122b to constrain the magnetic field from the first magnet 106 and the second magnet 116 about their periphery, thereby reducing flow of magnetic flux into the yoke 102, which is explained in detail in further sections of the description. In one configuration, the magnetization direction of the clamp members 122a, 122b is configured to be perpendicular to the magnetization direction of the first magnet 106 and the second magnet 116, respectively. In another configuration, the magnetization direction of the clamp members 122a, 122b may be oriented in the range of about 45 degrees to about 135 degrees to the magnetization direction of the first magnet 106 and the second magnet 116, respectively, for effective attenuation of the leakage flux flowing into the yoke 102.

In one configuration, mounting of the first clamp member 122a with the first magnet-pole assembly 104 refers to, engagement with the first magnet 106, the first pole shoe 108 and the first pole ring 110. As such, the engagement surface or inner surface (not shown in Figures) of the first clamp member 122a may be configured to match with the configuration of the outer surfaces (not shown in Figures) of the first magnet 106, the first pole shoe 108 and the first pole ring 110. This configuration ensures ease of mounting of the first clamp member 122a with the first magnet-pole assembly 104.

In another configuration, mounting of the second clamp member 122b with the second magnet-pole assembly 114 refers to, engagement with the second magnet 116, the second pole shoe 118 and the second pole ring 120. As such, the engagement surface or inner surface (not shown in Figures) of the second clamp member 122b is configured to match with the configuration of the outer surface (not shown in Figures) of the second magnet 116, the second pole shoe 118 and the second pole ring 120. This configuration ensures ease of mounting of the second clamp member 122b with the second magnet-pole assembly 114.

In one configuration, the clamp members 122a, 122b are configured with a tapered configuration or a wedge-shaped configuration, for the first magnet 106 and the second magnet 116 of uniform cylindrical cross-section, respectively. In this scenario, the thickness of the clamp members 122a, 122b is minimum towards the arms of the yoke 102, while the thickness is maximum at the periphery of the pole rings 110, 120. As such, the configuration of the clamp members 122a, 122b correspond to the configuration of the first magnet 106 and the second magnet 116, respectively. In another implementation, the configuration of the clamp members 122a, 122b is selected based on the magnetic flux required to be attenuated. In such scenarios, the thickness of the clamp members 122a, 122b may be minimum at areas where less magnetic flux is restricted and the thickness of the clamp member 122 may be maximum at areas where larger magnetic flux is restricted.

Figure 2A:
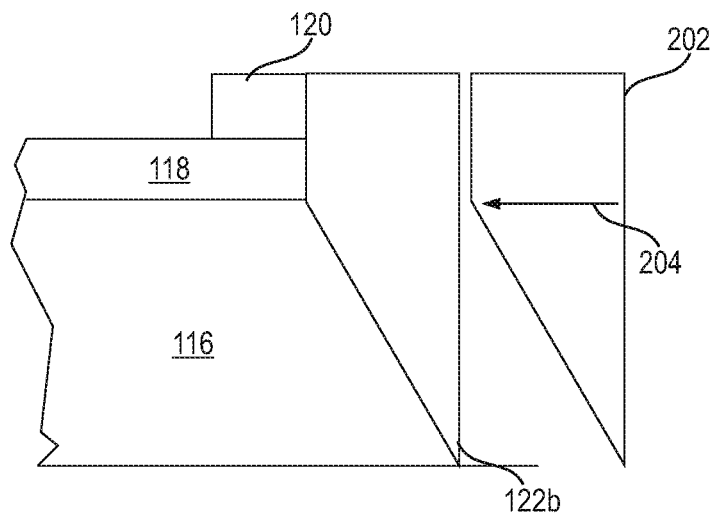
FIG. 2A is a schematic view depicting variation of a magnetic potential in the magnet assembly due to a clamp member, in accordance with an example embodiment of the present disclosure.

Referring to FIG. 2A in conjunction with FIG. 1B, an enlarged view of the second clamp member 122b mounted to the second magnet-pole assembly 114 and the associated magnetic interaction is illustrated. As illustrated, the magnetic field distribution (for e.g. referenced as '202' in FIG. 2B) is greater towards the second pole ring 120, due to conduction of the magnetic field by the second pole ring 120 from the second magnet 116. The magnetic field emanating from the second magnet 116 increases along the vertical distance of the second magnet-pole assembly 114. The clamp member 122b of tapered configuration is mounted to the second magnet-pole assembly 114. In this configuration, the second clamp member 122b is configured to be thicker towards the second pole ring 120 and thinner towards the medial surface 128a of the second arm 102c. This configuration is considered due to the magnetic flux of the second magnet 116 conducting towards the second pole ring 120, results in a higher magnetic potential or magnetic field towards the second pole ring 120. In other words, the configuration of the clamp member 122 corresponds to the magnetic potential of the respective magnet-pole assembly.

Upon engagement with the second magnet-pole assembly 114, the second clamp member 122b is configured to reduce the flow of flux emanating from the magnets to the yoke 102 at a pole region (for e.g. illustrated as reference '302' in FIG. 3A). The clamp member 122 prevents flow of magnetic flux to the yoke 102 due to its magnetization. The flow of magnetic flux into the yoke 102 is prevented due to constraint imposed by the magnetization of the second clamp member 122b. The magnetic flux that may flow into the yoke 102 is illustrated with arrow heads (for e.g. referenced as 204). Thus, the second clamp member 122b may act as a separation layer or an isolating layer for preventing flow of magnetic flux into the yoke 102. In one implementation, the magnetic flux flowing into the yoke 102 (or the leakage flux) may be computed using the following equation (Eq. 1).

$$\text{Leakage flux} = 1 - (GF/MF) \tag{Eq. 1}$$

Wherein, 'MF' is the total flux from the magnet, and 'GF' is the total flux across gap.

In another implementation, the magnetic flux flowing towards the pole ring (or the useful flux for imaging) may be computed using the following equation (Eq. 2).

$$\text{Useful flux} = (GF/MF) \tag{Eq. 2}$$

Wherein, 'MF' is the total flux from the magnet, and 'GF' is the total flux across gap.

The flux flowing from the magnet and the flux flowing across the gap may be determined via devices such as, but not limited to, magnetometer, computer simulation, or any other devices or techniques as per feasibility and requirement. From the computation, as illustrated in FIG. 3A, it is evident that the leakage flux is considerably reduced (leakage flux is 14%) upon mounting of the clamp member 122.

Figure 2B:
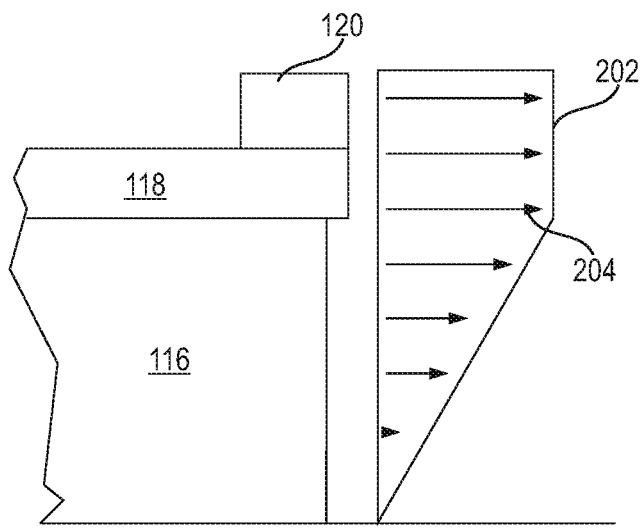
FIG. 2B is a schematic view depicting variation of the magnetic potential in a traditional magnet assembly, in accordance with an example embodiment of the present disclosure.
Figure 3B:
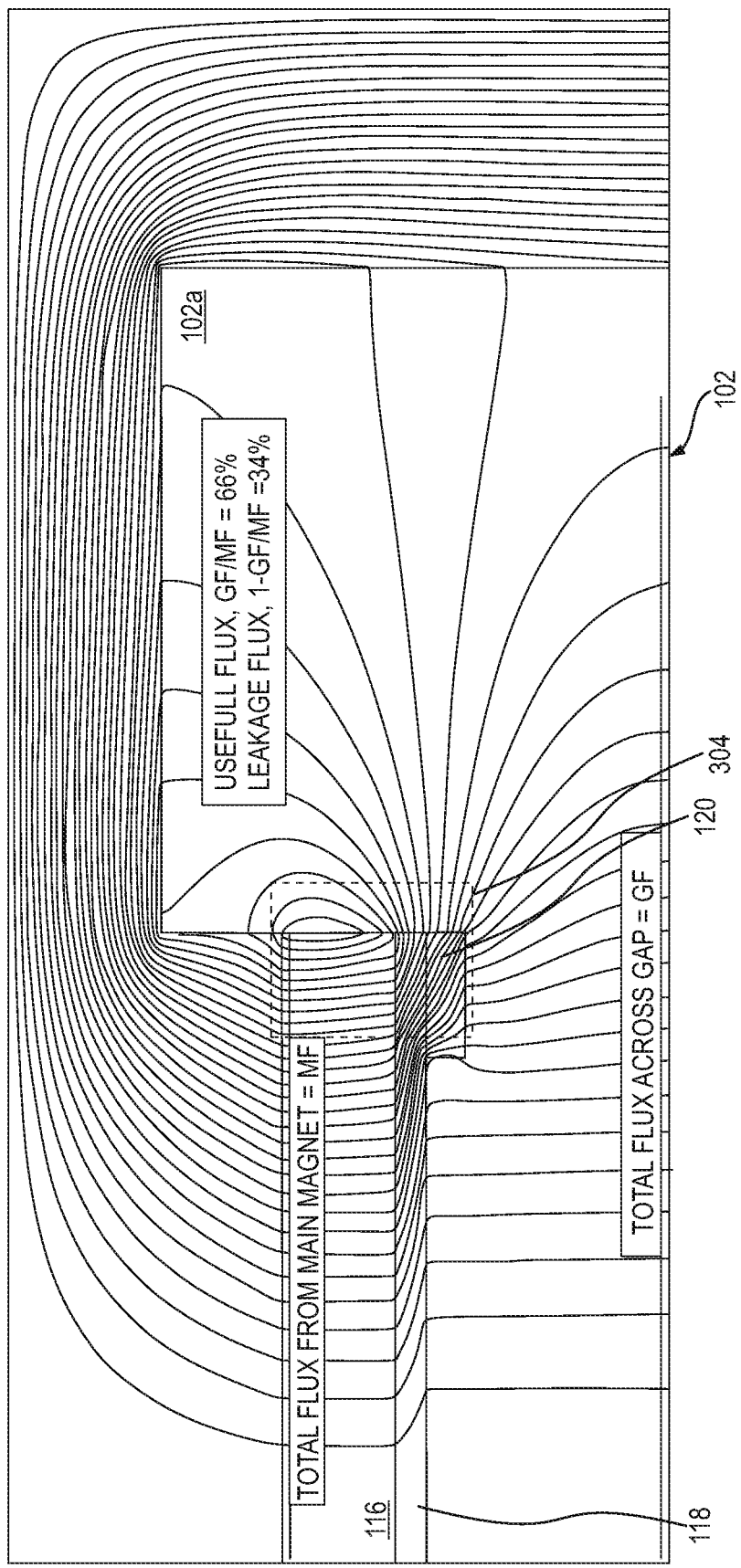
FIG. 3B is a schematic view depicting a magnetic field distribution in a traditional magnet assembly.

Referring to FIG. 2B in conjunction to FIG. 2A, the flow of magnetic flux into the yoke 102 without the second clamp member 122b is illustrated. As illustrated, the magnetic flux 204 flowing into the yoke 102 at the pole region is greater (indicated by a larger number of arrow heads), even though the magnetic potential 202 remains the same. Thus, it is evident that the magnet assembly 100 devoid of the second clamp member 122b is subjected to greater leakage flux (for e.g. illustrated as '304' in FIG. 3B), which may be due to direct contact of the surfaces of the magnets and poles with the yoke 102. Further, from the computation, as illustrated in FIG. 3B, it is evident that the leakage flux is considerably larger (leakage flux is 34%) without the clamp member 122.

The above reference of experimental observation pertaining to leakage flux, considered in view of the second magnet-pole assembly 114 and the second clamp member 122b are exemplary in nature and for the purpose of simplicity. It is understood that the same method, principles and techniques are applicable for the first magnet-pole assembly 104 and the first clamp member 122a as well, without departing from the scope of the present disclosure.

In one configuration, the clamp members 122a, 122b may be configured with the unibody construction or may be fabrication of plurality of pieces of the magnet material which may be mounted about the periphery of the magnet-pole assemblies, as per design feasibility and requirement. The permanent magnet material may be selected to be Neodymium Iron Boron (NdFeB) magnet material or any other material as per feasibility and requirement.

Referring back to FIG. 1B, a first retainer member 132a may be mounted to the first clamp member 122a and a second retainer member 132b may be mounted to the second clamp member 122b. The retainer members 132a, 132b are configured to maintain position of the clamp members 122a, 122b on the first magnet-pole assembly 104 and the second magnet-pole assembly 114 respectively. The retainer members 132a, 132b may conform to the shape and configuration of the clamp members 122a, 122b, so that the retainer members 132a, 132b may snugly engage with the clamp members 122a, 122b, for locking the clamp members 122a, 122b onto the respective magnet-pole assemblies 104, 114. The retainer members 132a, 132b may engage with the clamp members 122a, 122b via conventional means, such as, but not limited to, fastening, bonding, gluing and the like as per requirement. The retainer members 132a, 132b may be made of a metallic material or a non-metallic material as per requirement.

Figure 4A:
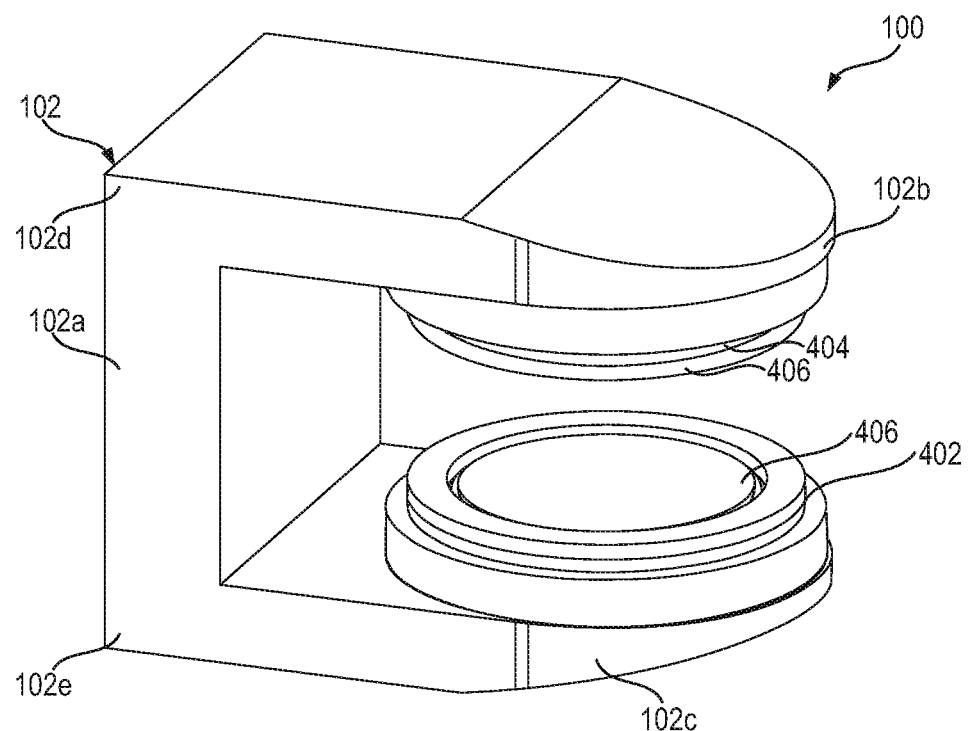
FIG. 4A is a perspective view of the magnet assembly comprising an eddy current control plate, in accordance with an example embodiment of the present disclosure.
Figure 4B:
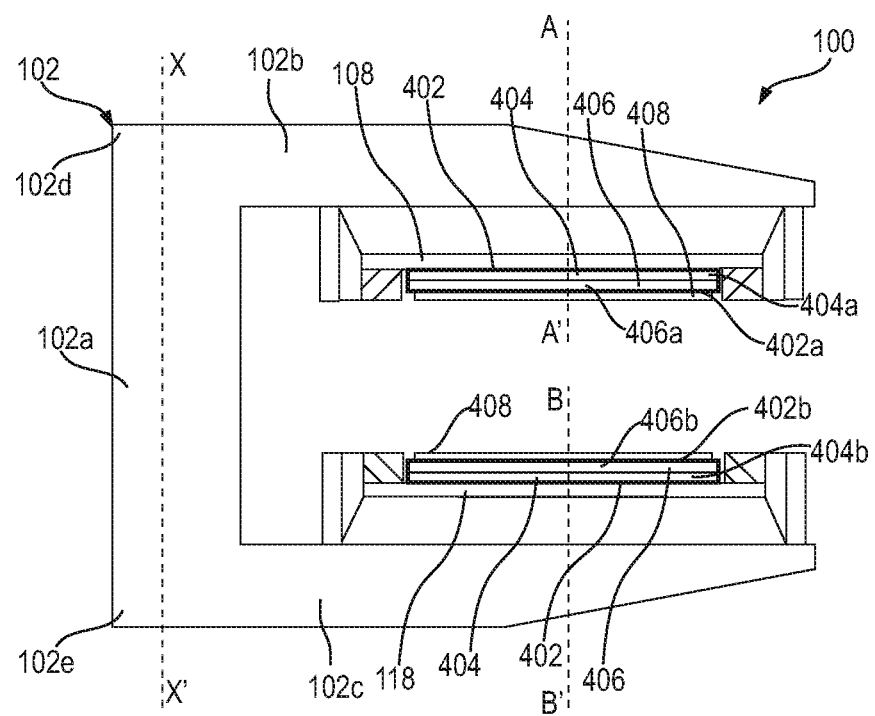
FIG. 4B is a cross section view of the magnet assembly comprising the eddy current control plate, in accordance with an example embodiment of the present disclosure.

FIGS. 4A and 4B, in one exemplary embodiment of the present disclosure, illustrate the magnet assembly 100, including an eddy current control plate 402. The eddy current control plate 402 is configured to attenuate formation of eddy currents during use of the magnet assembly 100, while also boosting the magnetic field of the magnet assembly 100.

The eddy current control plate 402 may be a plate structure, bonded to each of the first pole shoe 108 and the second pole shoe 118. For ease of understanding, the control plate 402 mounted to the first pole shoe 108 is denoted by reference '402a' and the control plate 402 mounted to the second pole shoe 118 is denoted by reference '402b'. The control plate 402 is mounted about the central portion or the portion between the extension of the pole rings 110, 120. The control plate 402 may be mounted via conventional mounting means selected from one of gluing, fastening, clamping, bonding or any other technique as per requirement.

The control plate 402 comprises a permeable layer 406 (Eddy current control plate), which can be a laminated amorphous silicon-iron layer, bonded over a magnetic material layer 404 which is a Flux Saturation Control Plate (FSCP). This results in the FSCP magnetic layer 404 lowering the saturation of the amorphous silicon iron while boosting the main magnet field. The amorphous silicon iron layer 406 prevents formation of eddy currents in the magnets due to its high permeability. For ease of understanding, the FSCP magnetic layer 404 mounted to the first pole shoe 108 is denoted by reference '404a' and the FSCP magnetic layer 404 mounted to the second pole shoe 118 is denoted by reference '404b'. Similarly, for ease of understanding, the permeable layer 406 mounted to the magnetic layer 404a is denoted by reference '406a' and the permeable layer 406 mounted to the magnetic layer 404b is noted by reference '406b'.

The FSCP magnetic layer 404 upon mounting, boosts or amplifies the magnetic field of the magnet due to its magnetization, while also lowering the saturation of the silicon-iron layer. Additionally, the magnetic layer 404 spaces the highly permeable silicon-iron layer from the pole shoe for effective dissipation or attenuation of the eddy currents.

In one configuration, the permeable layer 406 on the control plate 402 may be replaced with other permeable materials, which can attenuate the eddy currents generated during the use of the magnet assembly 100. In one configuration, the magnetic material 404 may be a unibody construction or may be a tiled layer made of suitable permanent magnetic material as per requirement.

In an embodiment, a gradient coil 408 may be mounted to the control plate 402. The gradient coil 408 may be configured to alter the magnetic field received from the magnets predictably, which enables spatial encoding of the magnetic field. In one configuration, the gradient coil 408 may be the magnetic coil typically employed in traditional MRI scanners for altering the magnetic fields.

Figure 5A:
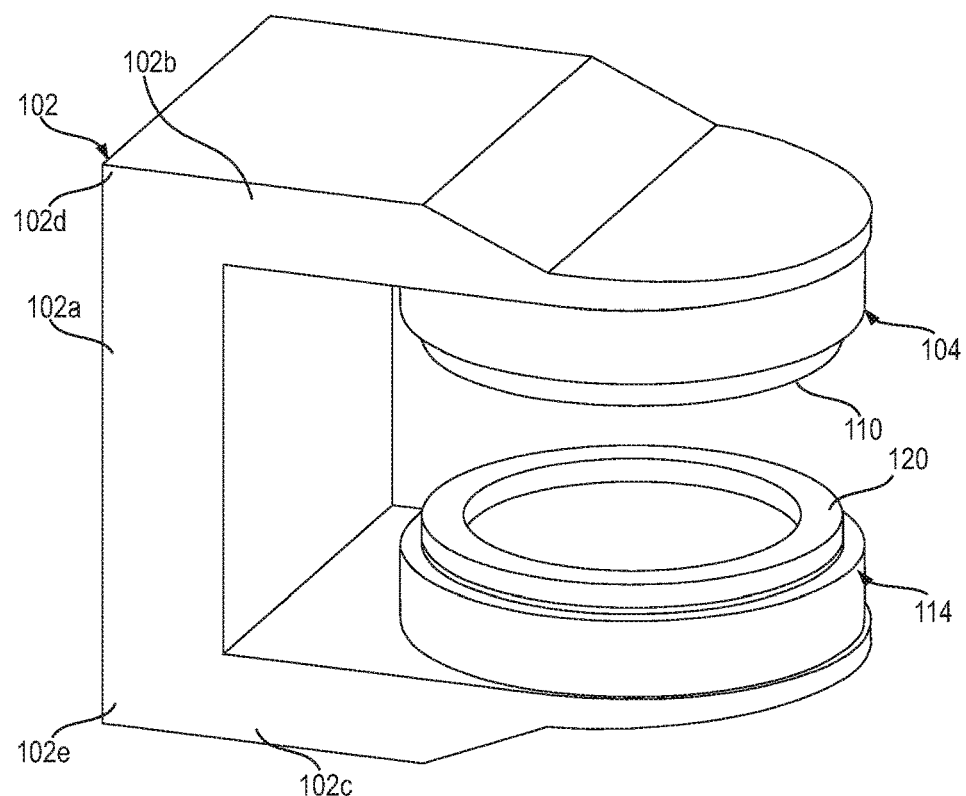
FIG. 5A is a perspective view of the magnet assembly, in accordance with another example embodiment of the present disclosure.
Figure 5B:
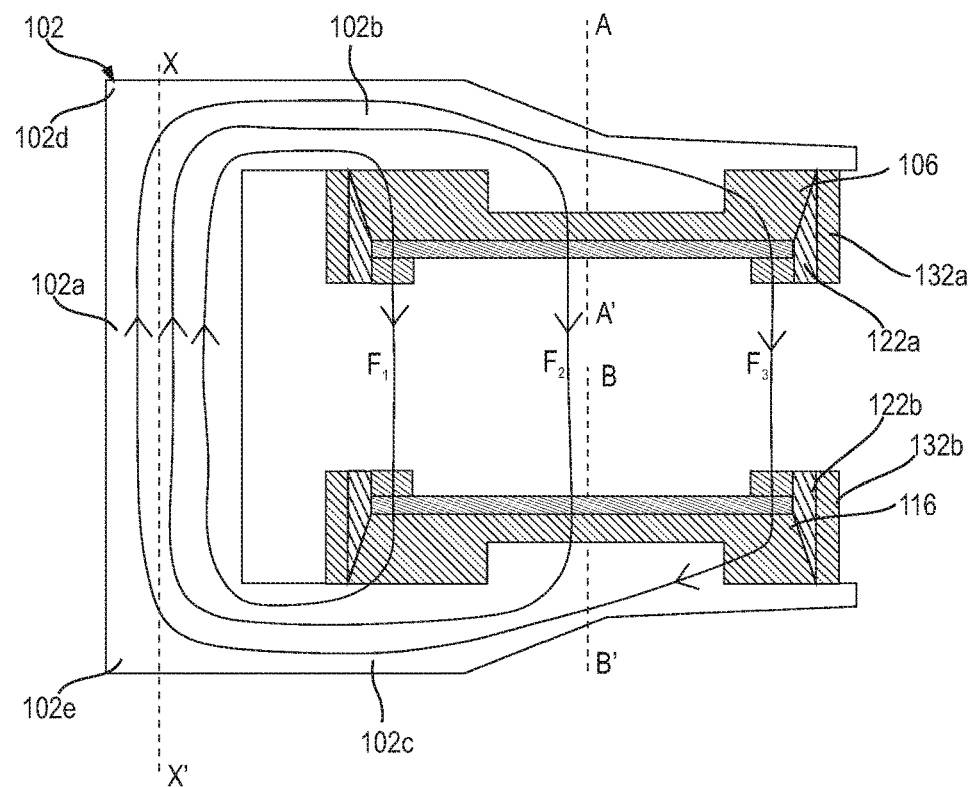
FIG. 5B is a schematic view of the magnet assembly of FIG. 5A, in accordance with an example embodiment of the present disclosure.

All prior MRI magnets are made with a uniform thickness of the magnets. FIGS. 5A and 5B, in one exemplary embodiment of the present disclosure, illustrate the magnet assembly 100 employing non-uniform configuration of the magnets. That is, the first magnet 106 and the second magnet 116 are configured with a non-uniform thickness. The magnet-pole assemblies having a nonuniform layer of magnet material that in the center quarter of the diameter or width of the magnet-pole assemblies 104, 114. In an embodiment, the thickness of the magnet material is less than 0.8 times the thickness of magnet material at the periphery of the magnet-pole assemblies. As such, the configurations of the medial surfaces 126a, 128a are also altered to conform to the configuration of the magnets.

In this configuration, the magnets (i.e. the first magnet 106 and the second magnet 116) are configured with reduced thickness about the first and the second central axes A-A', B'B'. As such, the magnetic flux density emanating at the center is low compared to the magnetic flux density at the radial ends. As an example, if F1 and F3 are considered to be the magnetic flux density at the radial ends of the magnets and F2 is the magnetic field along the central axis, it is imperative that the F1 and F3 are greater in magnitude than F2. Accordingly, the size and configuration of the pole ring and the thickness of the magnets (106 and 116) may be altered based on the amount of magnetic field to be conducted. Employing a non-uniform configuration of the magnets reduces the CPT 802 as defined below, making a more compact magnet. This is because flux F1 does not traverse into the central axes, allowing 102b and 102c to be thinner at the central axis due to the reduced amount of flux at the central axis, and additionally the magnets at the central axis are thinner. In prior MRI magnets, a portion of F1 will traverse into the central axis, requiring more thickness to conduct the additional flux.

In one implementation, the first magnet 106 may be a magnet with uniform thickness, while the second magnet 116 may be a magnet with non-uniform thickness. In such scenarios, the configuration of the associated pole ring is selected as per the magnetic field strength required for imaging the body portion 708 of the subject 610.

In one implementation, the first magnet 106 may be a magnet with non-uniform thickness, while the second magnet 116 may be a magnet with uniform thickness. In such scenarios, the configuration of the associated pole rings is selected as per the magnetic field strength required for imaging the body portion 708 of the subject 610.

FIG. 6, in one exemplary embodiment of the present disclosure, illustrates the magnet assembly 100, with the magnets fabricated via the plurality of magnetic blocks 602. For bonding the plurality of magnetic blocks 602, a base layer 604 of identical material to 102 (i.e. a ferrous material that conducts magnetic flux) may initially be mounted onto the arms 102b, 102c of the yoke 102. Thereafter, the plurality of magnetic blocks 602 are arranged in order around the base layer 604 and bonded suitably. The subject 610 is positioned in the gap defined between the first magnet-pole assembly 104 and the second magnet-pole assembly 114. The positioning of the subject 610 typically depends on the body portion 708 that is required to scanned or imaged. However, for optimum scanning, the subject 610 is required to be positioned between the pole rings 110, 120 of the magnets.

Further, the arms 102b and 102c may be configured with hook members 608 for ensuring mounting and/or transporting the magnet assembly 100. In one implementation, the hook members 608 may be connectable with a cable-pulley mechanism (not shown in Figures), for enabling movement of the frame member 102a over the guiderail 607. The hook members 608 may be positioned at suitable locations on the arms 102b, 102c for ensuring safety and stability during movement and/or transportation.

In one implementation, the frame member 102a may be rotatably mounted on to the guiderail 607 via bearings or any other suitable means as per requirement. This allows the magnet gap to be rotated parallel with the floor member 702 between a first angle position and a second angle position (not shown in Figures). The first angle position may be the position at which the frame member 102a is positioned below the floor member 702, while the second angle position may be the position at which the frame member 102a is positioned parallel to the floor member 702. This way an anesthetized animal can be brought in a gurney and allow the animal's leg to be imaged (not shown in any figure). The frame member 102a may be connected to a suitable mechanism, herein called the magnet movement unit (MMU), such as but not limited to a hydraulic actuator mechanism, a pneumatic actuator mechanism and the like, for operation between the first position 704 and the second position 706 (for e.g. as shown in FIG. 7B). In one configuration, the MMU 606 may be operated suitably, so that the magnet assembly 100 attains the first position 704 and the second position 706.

FIGS. 7A and 7B in one exemplary embodiment of the present disclosure, illustrate the magnet assembly 100 employed for scanning the body portion 708 of the subject 610. In one implementation, the subject 610 is a horse or an equine and the body portion 708 to be scanned is a limb of the horse.

Prior to the initiation of the scanning procedure, the horse is sedated by a medical practitioner (not shown in Figures) and is positioned on the floor member 702. The floor member 702 may act as a platform for resting the magnet assembly 100 suitably. The magnet assembly 100 is initially at a rest position or the first position 704, with the arms 102b, 102c resting on the floor member 702. At this position, the horse is positioned on the floor member 702 such that the limb to be scanned is placed between the arms 102b, 102c (for e.g. as shown in FIG. 7A).

Figure 8:
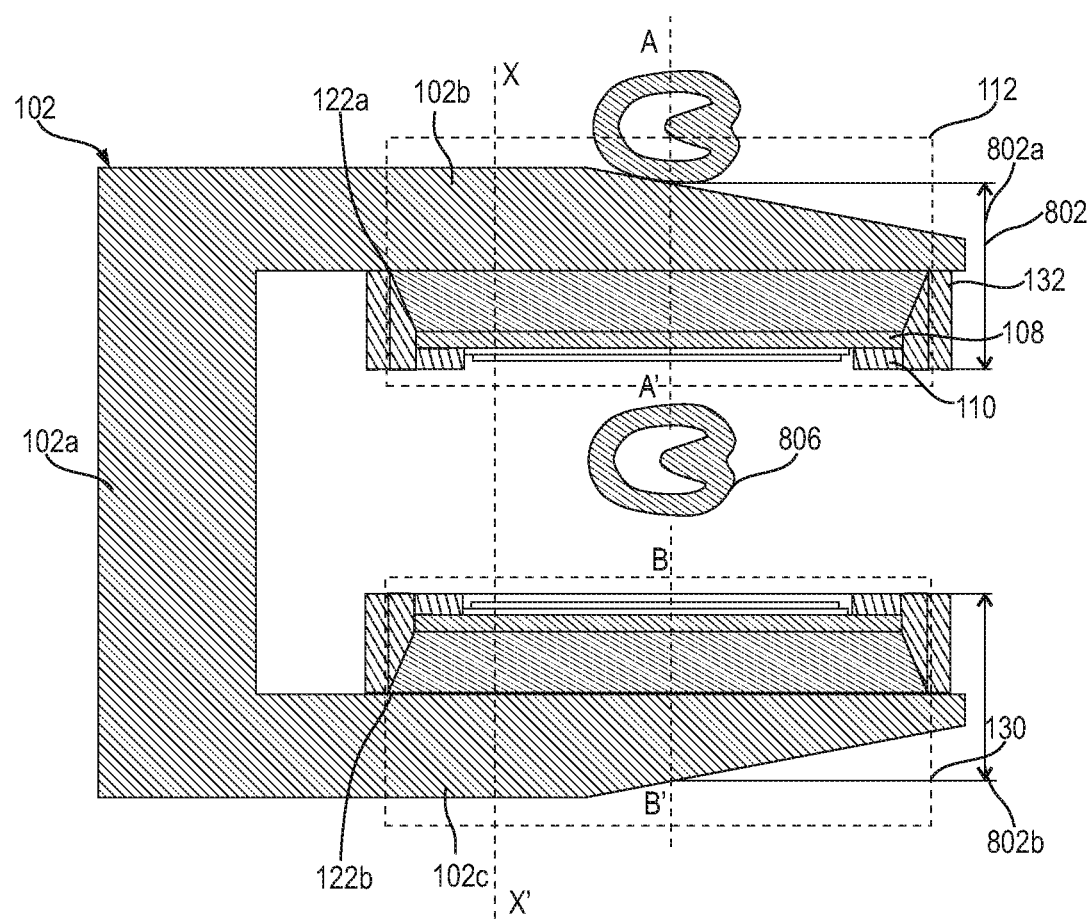
FIG. 8 is a schematic view of the magnet assembly, depicting a Center Pole Thickness (CPT) of a first pole and a second pole, in accordance with an example embodiment of the present disclosure.

Referring to FIG. 8 in conjunction with FIGS. 7A and 7B, the position of the limb (or the body portion 708) is determined based on a center pole thickness 802 (hereinafter referred to as 'CPT 802') of the magnet assembly 100. The CPT 802 is the combined thickness of the arm of the yoke 102, the magnet, the pole shoe and the pole ring, about the central axis of the magnets. For ease of understanding, the CPT 802 is referenced as '802a' for the thickness of the first pole 112 and the CPT 802 is referenced as '802b' for the thickness of the second pole 130. Further, the CPT 802 also defines the maximum thickness that the size and configuration of the magnet assembly 100 may be selected for scanning a horse. Typically, the horse while standing naturally tends to keep its feet together, which may be approximately 7 inches or 177.8 mm apart. Thus, the CPT 802 is required to be less than 7 inches for enabling use of the magnet assembly 100 for scanning the limbs. In one implementation, based on the CPT 802, the body portion 708 is positioned in a mid-plane or in the middle of the gap defined between the first pole 112 and the second pole 130. This placement ensures uniform magnetization of the body portion 708.

For reducing the CPT 802, the pole thickness i.e. the thickness of the arm, the magnet, the pole shoe and the pole ring is required to be minimum, without altering the magnetic properties of the magnet assembly 100. As such in the present disclosure, the engagement of the clamp member 122a and 122b with the magnet-pole assembly ensures higher magnetic performance than the traditional systems, which enables to reduce the pole thickness as per requirement. In one configuration, the lateral surfaces 126b and 128b are configured with stepped profile or tapered profile for reducing the CPT 802. In one implementation, the performance of the magnet assembly 100 is improved from 0.26 to 0.4 Tesla due to the introduction of the clamp member 122a, 122b.

Referring back to FIGS. 7A and 7B, upon positioning the body portion 708 of the horse between the arms 102b, 102c, the magnet assembly 100 is initiated for scanning. Upon completion of the scanning in the first position 704, the magnet assembly 100 is moved further up the limb until the 706. For moving the magnet assembly 100, the frame member 102a may be operated suitably to the second position 706 (as shown in FIG. 7B). The second position 706 may be the position at the vicinity of the torso of the horse. In one implementation, the second position 706 may be adjusted based on a pole size 712 of the magnet assembly 100. The pole size 712 may be size of width of the poles of the magnet assembly 100. In one configuration, the pole size 712 may be referred to as a pole diameter for cylindrical poles configured in the magnet assembly 100. The pole size 712, similar to the CPT 802, depends on the magnetic performance of the magnet assembly 100. Thus, when the magnetic performance of the magnet assembly 100 is high, a corresponding reduction in the pole size 712 may be achieved. This configuration inherently affects the reachability or access to the limb of the horse.

FIG. 9 in one exemplary embodiment of the present disclosure illustrates a schematic view of an equine MRI system 900, employing the magnet assembly 100. The system 900 is configured to monitor the magnetization of the body portion 708 and generate the visual representation of the anatomy of the body portion 708. The system 900 is configured to operate as per conventional MRI systems.

The system 900 includes a computing device 902 associated with the magnet assembly 100, via a spectrometer 904, a gradient amplifier 906, an RF amplifier 908. The spectrometer 904, the gradient amplifier 906 and the RF amplifier 908 are suitably coupled to the magnet assembly 100, for transmitting waveforms and receiving signals during imaging of the body portion 708. As such, the gradient amplifier 906 transmits waveforms to the gradient coil 408. The RF amplifier 908 may be configured to transmit waveforms to the magnet-pole assembly, while the spectrometer 904 may receive signals from the body portion 708. The computing device 902 is configured to control operations of the magnet assembly 100 i.e. movement between the first position 704 and the second position 706, controlling imaging positions and the like.

Upon receiving the signals, the computing device 902 may process and/or manipulate the signals suitably for generating the visual representation. In one implementation, the computing device 902 may be configured with suitable hardware and software components for processing and generating the visual representation of the anatomy of the body portion 708.

In one embodiment, the magnet assembly 100 may also be employed in the traditional MRI system for scanning the body portion 708.

In an embodiment, the medial surfaces 106b and 116a are the surfaces oriented parallel to a median plane defined with respect to the frame member 102a (not shown in figures). In one configuration, the medial surfaces 106b and 116a may be positioned proximal to the median plane of the frame member 102a. In another embodiment, the lateral surfaces 126b and 128b may be top surfaces of the first arm 102b and the second arm 102c. In one configuration, the lateral surfaces 126b and 128b may be surfaces which are positioned away from the median plane of the frame member 102a. In yet another embodiment, the exposed surface of the pole rings 110 and 120 may be the surfaces exposed to the median plane of the frame member 102a (not shown in figures).

The benefits and advantages described above may relate to one embodiment or may relate to several embodiments. The embodiments are not limited to those that solve any or all of the stated problems or those that have any or all of the stated benefits and advantages.

The above description is given by way of example only and various modifications may be made by those skilled in the art. The above specification, examples and data provide a complete description of the structure and use of exemplary embodiments. Although various embodiments have been described above with a certain degree of particularity, or with reference to one or more individual embodiments, those skilled in the art could make numerous alterations to the disclosed embodiments without departing from the spirit or scope of this specification.

What is claimed is:

1. An equine Magnetic Imaging Resonance (MRI) system, the equine MRI system comprising:
   a magnet assembly, comprising:
      a frame member movably positioned relative to a floor by a magnet movement unit (MMU), the frame member including a first end and a second end,
      a first arm extending laterally from the first end of the frame member and including a first magnet-pole assembly, the first magnet-pole assembly comprising a first central axis, a first magnet, a first pole shoe, and a first pole ring,
      a second arm extending laterally from the second end and including a second magnet-pole assembly, the second magnet-pole assembly comprising a second central axis, a second magnet, a second pole shoe, and a second pole ring, and configured to orient towards the first magnet-pole assembly while maintaining a gap therebetween, for positioning a body portion of a subject,
      a first clamp member and a second clamp member mounted about a peripheral side surface of the first magnet-pole assembly and the second magnet-pole assembly, respectively, the first and the second clamp members oriented to attenuate a leakage flux emanating from the first magnet-pole assembly and the second magnet pole-assembly, respectively, and
      the magnet-pole assemblies having a non-uniform first magnet and a non-uniform second magnet, wherein the thickness of the non-uniform first magnet in the center of the first magnet-pole assembly is less than the thickness of the non-uniform first magnet at the periphery of the first magnet-pole assembly and wherein the thickness of the non-uniform second magnet in the center of the second magnet-pole assembly is less than the thickness of the non-uniform second magnet at the periphery of the second magnet-pole assembly.

2. The equine MRI system as claimed in claim 1, further comprising a guide rail extending laterally from the magnet movement unit (MMU), the guide rail configured to rotatably receive the frame member, wherein the guide rail is configured to allow rotational movement of the frame member from the MMU, between a first angle position and a second angle position.

3. The equine MRI system as claimed in claim 1, wherein the first magnet-pole assembly comprises:
   the first magnet including a top surface and a medial surface, the top surface of the first magnet mounted to the medial of the first;
   the first pole shoe mounted along a periphery of the medial surface of the first magnet; and
   the first pole ring mounted to the first pole shoe, and wherein the second magnet-pole assembly comprises:
   the second magnet including a medial surface and a bottom surface, the bottom surface of the second magnet mounted to the medial surface of the second arm;
   the second pole shoe mounted along a periphery of the medial surface of the second magnet; and
   the second pole ring mounted to the second pole shoe.

4. The equine MRI system as claimed in claim 1, further comprising a flux saturation control plate (FSCP) made of a permanent magnet material and mounted onto each of a first pole shoe and a second pole shoe, wherein an eddy current control plate is mounted onto the Flux Saturation Control Plate (FSCP), the FSCP is oriented to increase main field of a magnet configured in each of the first magnet-pole assembly and a second magnet-pole assembly.

5. The equine MRI system as claimed in claim 1, wherein configuration of the first and the second clamp members are thinner near a medial surface of a yoke and are thicker away from the medial surface of the yoke.

6. The equine MRI system as claimed in claim 1, wherein the first and the second clamp members are magnetized in a direction perpendicular to a magnetization direction of the first magnet-pole assembly and the second magnet-pole assembly, respectively.

7. The equine MRI system as claimed in claim 1 further comprising, a first retainer member and a second retainer member mounted on the first and the second clamp members, the first and the second retainer members configured to maintain position of the first and the second clamp members on the first magnet-pole assembly and the second magnet-pole assembly, respectively.

8. The equine MRI system as claimed in claim 1, further comprising a computing device of the equine MRI system connectable to the first magnet-pole assembly, the second magnet-pole assembly and the body portion, the computing device configured to process magnetic field interaction of the body portion positioned between the first magnet-pole assembly and the second magnet-pole assembly for generating an image of an anatomy of the body portion.

* * * * *